US011254689B2

(12) United States Patent
Porras De Francisco et al.

(10) Patent No.: US 11,254,689 B2
(45) Date of Patent: Feb. 22, 2022

(54) COMPOUNDS

(71) Applicants: GLAXOSMITHKLINE INTELLECTUAL PROPERTY DEVELOPMENT LIMITED, Brentford (GB); BIOVERSYS AG, Basel (CH)

(72) Inventors: Esther Porras De Francisco, Madrid (ES); Modesto Jesús Remuiñan-Blanco, Madrid (ES); Marilyne Bourotte, Perenchies (FR); Benoit Deprez, Lille (FR); Nicolas Willand, Lille (FR)

(73) Assignees: GLAXOSMITHKLINE INTELLECTUAL PROPERTY DEVELOPMENT LIMITED, Brentford (GB); BIOVERSYS AG, Basel (CH)

( * ) Notice: Subject to any disclaimer, the term of this patent is extended or adjusted under 35 U.S.C. 154(b) by 0 days.

(21) Appl. No.: 16/639,192

(22) PCT Filed: Aug. 15, 2018

(86) PCT No.: PCT/EP2018/072143

§ 371 (c)(1),
(2) Date: Feb. 14, 2020

(87) PCT Pub. No.: WO2019/034700

PCT Pub. Date: Feb. 21, 2019

(65) Prior Publication Data

US 2021/0032268 A1 Feb. 4, 2021

(30) Foreign Application Priority Data

Aug. 16, 2017 (EP) .................................... 17382569

(51) Int. Cl.
*C07D 498/10* (2006.01)
*A61P 31/06* (2006.01)
*A61K 45/06* (2006.01)

(52) U.S. Cl.
CPC ............ *C07D 498/10* (2013.01); *A61P 31/06* (2018.01); *A61K 45/06* (2013.01)

(58) Field of Classification Search
CPC ........ C07D 498/10; A61P 31/06; A61K 45/06
USPC .......................................................... 514/278
See application file for complete search history.

(56) References Cited

U.S. PATENT DOCUMENTS

2006/0094767 A1 5/2006 Tsubouchi et al.

FOREIGN PATENT DOCUMENTS

WO 2014/096369 A1 6/2014

OTHER PUBLICATIONS

Blondiaux, et al. "Reversion of antibiotic resistance in *Mycobacterium tuberculosis* by spiroisoxazoline SMARt-420". Science, vol. 355, pp. 1206-1211 (Mar. 17, 2017).
Kai Lv, et al. "Identification of better pharmacokinetic benzothiazinone derivatives as new antitubercular agents". ACS Medicinal Chemistry Letters, 8(6): 636-641 (May 12, 2017).
Srivastava, et al. "Synthesis and biological evaluation of 4-thiazolidinone derivatives as potential antimycobacterial agents". ARKIVOC, 2005(2): 120-130 (Mar. 16, 2005).
Tantry, Subramanyam, et al. "Whole cell screen based identification of spiropiperidines with potent antitubercular properties". Bioorganic & Medicinal Chemistry Letters, 25(16): 3234-3245 (Aug. 2015).

*Primary Examiner* — Kristin A Vajda
(74) *Attorney, Agent, or Firm* — Robert H. Brink; Scott Young; Duke M. Fitch

(57) ABSTRACT

The invention relates to compounds of Formula (I) and their use in therapy, for example in the treatment of mycobacterial infections or in the treatment of diseases caused by *mycobacterium*, such as tuberculosis.

(I)

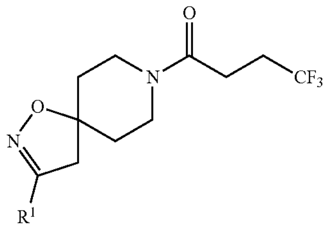

28 Claims, No Drawings

COMPOUNDS

This application is a § 371 of International Application No. PCT/EP2018/072143, filed 15 Aug. 2018, which claims the priority of EP 17382569.6, filed 16 Aug. 2017.

FIELD OF THE INVENTION

The invention relates to novel compounds, compositions containing them, and their use in therapy, for example in the treatment of mycobacterial infections or in the treatment of diseases caused by *mycobacterium*, such as tuberculosis (also known as TB).

BACKGROUND TO THE INVENTION

Nearly ten million people are infected with tuberculosis (TB) each year, causing 1.5 million deaths each year, according to a report published by The World Health Organisation in 2014. Despite available treatments for tuberculosis, incidence of the disease still begins to rise, owing to infection by *Mycobacterium tuberculosis*, the causative bacterial agent for TB, becoming resistant to many of the first-line treatments such as isoniazid and rifampicin.

Ethionamide, a structural analogue of isoniazid, is frequently prescribed for the treatment of multidrug-resistant TB (MDR TB), which is as efficient as isoniazid. However, a disadvantage associated with the use of ethionamide is that in order to obtain an acceptable concentration of the drug in the blood, up to 1 g/day is required, which is associated with severe side effects including neurotoxicity and fatal hepatotoxicity. Therefore, there exists a need to reduce the clinical dose and exposure to ethionamide.

Consequently, one aim of the present invention is to provide novel compounds that are likely to be able to potentiate the activity of drugs used in the treatment of TB, in particular drugs that are activatable via the EthA pathway, such as ethionamide. A further aim of the present invention is to provide novel compounds for the treatment of TB.

PCT publication number WO 2014/096369 describes spiroisoxazoline compounds bearing an aryl, cycloalkyl or heteroaryl substituent group. Such compounds are said to be useful in the treatment of TB.

SUMMARY OF THE INVENTION

In a first aspect of the present invention there is provided a compound of Formula (I):

(I)

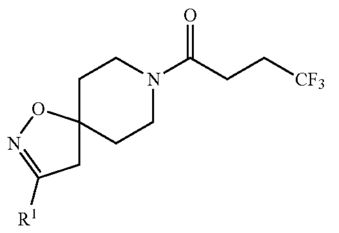

wherein $R^1$ is halogen; cyano; $C_{1-6}$ straight alkyl; $C_{3-4}$ branched alkyl; $C_{1-6}$ straight alkoxy; $C_{3-4}$ branched alkoxy; methyl substituted by one or more fluoro; ethyl substituted by one or more fluoro; methoxy substituted by one or more fluoro; or ethoxy substituted by one or more fluoro; or a pharmaceutically acceptable salt thereof.

In a second aspect of the invention, there is provided a compound of Formula (I), or pharmaceutically acceptable salt thereof, for use in therapy, in particular for use in the treatment of tuberculosis.

In a third aspect of the invention, there is provided a method for the treatment of a mycobacterial infection in a mammal in need thereof, comprising administering to said mammal a therapeutically effective amount of a compound of Formula (I) or a pharmaceutically acceptable salt thereof.

In a fourth aspect of the invention, there is provided a method for the treatment of a disease caused by infection with a *mycobacterium* in a mammal in need thereof, comprising administering to said mammal a therapeutically effective amount of a compound of Formula (I), or a pharmaceutically acceptable salt thereof.

In a fifth aspect of the invention, there is provided the use of a compound of Formula (I), or a pharmaceutically acceptable salt thereof, in the manufacture of a medicament for use in the treatment of a mycobacterial infection or a disease resulting caused by infection with a *mycobacterium*.

In a sixth aspect of the invention, there is provided a compound of Formula (I), or pharmaceutically acceptable salt thereof, for use in the treatment of a mycobacterial infection or for use in the treatment of a disease caused by infection with a *mycobacterium*.

In a seventh aspect of the invention, there is provided a pharmaceutical composition comprising (a) a compound of Formula (I) or pharmaceutically acceptable salt thereof; and (b) a pharmaceutically acceptable excipient.

In an eighth aspect of the invention, there is provided a combination of (a) a compound of Formula (I) or pharmaceutically acceptable; and (b) at least one other anti-mycobacterial agent.

DETAILED DESCRIPTION OF THE INVENTION

As described above, one aspect the invention relates to a compound of Formula (I) or pharmaceutically acceptable salt thereof:

(I)

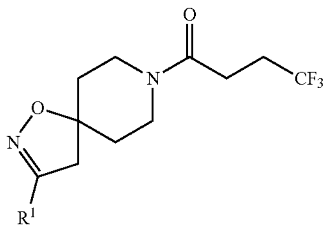

wherein $R^1$ is halogen; cyano; $C_{1-6}$ straight alkyl; $C_{3-4}$ branched alkyl; $C_{1-6}$ straight alkoxy; $C_{3-4}$ branched alkoxy; methyl substituted by one or more fluoro; ethyl substituted by one or more fluoro; methoxy substituted by one or more fluoro; or ethoxy substituted by one or more fluoro.

In one embodiment, the invention relates to a compound of Formula (I).

In one embodiment, $R^1$ is fluoro, chloro or bromo; cyano; $C_{1-6}$ straight alkyl; $C_{3-4}$ branched alkyl; $C_{1-6}$ straight alkoxy; $C_{3-4}$ branched alkoxy; methyl substituted by one or more fluoro; ethyl substituted by one or more fluoro; methoxy substituted by one or more fluoro; or ethoxy substituted by one or more fluoro.

In one embodiment, $R^1$ is fluoro, chloro or bromo; cyano; $C_{1-6}$ straight alkyl; $C_{3-4}$ branched alkyl; $C_{1-6}$ straight alkoxy; $C_{3-4}$ branched alkoxy; mono-, di- or trifluoromethyl; mono-, di- or trifluoromethoxy; 2-fluoroethyl; 2,2-difluoroethyl; 2,2,2-trifluoroethyl; 2-fluoroethoxy, 2,2-difluoroethoxy; or 2,2,2-trifluoroethoxy.

In one embodiment, $R^1$ is chloro or bromo; cyano; $C_{1-6}$ straight alkyl; $C_{3-4}$ branched alkyl; $C_{1-6}$ straight alkoxy; $C_{3-4}$ branched alkoxy; mono-, di- or trifluoromethyl; mono-, di- or trifluoromethoxy; 2-fluoroethyl; 2,2-difluoroethyl; 2,2,2-trifluoroethyl; 2-fluoroethoxy, 2,2-difluoroethoxy; or 2,2,2-trifluoroethoxy.

In one embodiment, $R^1$ is fluoro, chloro, bromo, cyano, $C_{1-6}$ straight alkyl, $C_{3-4}$ branched alkyl, $C_{1-6}$ straight alkoxy, $C_{3-4}$ branched alkoxy, trifluoromethyl, trifluoromethoxy, 2,2,2-trifluoroethyl or 2,2,2-trifluoroethoxy.

In one embodiment, $R^1$ is chloro, bromo, cyano, $C_{1-6}$ straight alkyl, $C_{3-4}$ branched alkyl, $C_{1-6}$ straight alkoxy, $C_{3-4}$ branched alkoxy, trifluoromethyl, trifluoromethoxy, 2,2,2-trifluoroethyl or 2,2,2-trifluoroethoxy.

In one embodiment, $R^1$ is fluoro, chloro, bromo, cyano, $C_{1-6}$ straight alkyl, $C_{3-4}$ branched alkyl, $C_{1-6}$ straight alkoxy, $C_{3-4}$ branched alkoxy, trifluoromethyl, 2,2,2-trifluoroethyl or 2,2,2-trifluoroethoxy.

In one embodiment, $R^1$ is chloro, bromo, cyano, $C_{1-6}$ straight alkyl, $C_{3-4}$ branched alkyl, $C_{1-6}$ straight alkoxy, $C_{3-4}$ branched alkoxy, trifluoromethyl, 2,2,2-trifluoroethyl or 2,2,2-trifluoroethoxy.

In one embodiment, $R^1$ is fluoro, bromo, cyano, $C_{1-4}$ straight alkyl, $C_{1-6}$ straight alkoxy, $C_4$ branched alkoxy, trifluoromethyl, 2,2,2-trifluoroethyl or 2,2,2-trifluoroethoxy.

In one embodiment, $R^1$ is bromo, cyano, $C_{1-4}$ straight alkyl, $C_{1-6}$ straight alkoxy, $C_4$ branched alkoxy, trifluoromethyl, 2,2,2-trifluoroethyl or 2,2,2-trifluoroethoxy.

In one embodiment $R^1$ is fluoro, bromo, cyano, methyl, ethyl, trifluoromethyl, 2,2,2-trifluoroethoxy, methoxy, ethoxy, n-propoxy, iso-butoxy or hexyloxy.

In one embodiment $R^1$ is bromo, cyano, methyl, ethyl, trifluoromethyl, 2,2,2-trifluoroethoxy, methoxy, ethoxy, n-propoxy, iso-butoxy or hexyloxy.

In one embodiment, $R^1$ is trifluoromethyl.

Particular compounds which are useful in the present invention include:

4,4,4-trifluoro-1-[3-(2,2,2-trifluoroethoxy)-1-oxa-2,8-diazaspiro[4.5]dec-2-en-8-yl]butan-1-one;

4,4,4-trifluoro-1-(3-propoxy-1-oxa-2,8-diazaspiro[4.5]dec-2-en-8-yl)butan-1-one;

4,4,4-trifluoro-1-(3-isobutoxy-1-oxa-2,8-diazaspiro[4.5]dec-2-en-8-yl)butan-1-one;

4,4,4-trifluoro-1-(3-hexyloxy-1-oxa-2,8-diazaspiro[4.5]dec-2-en-8-yl)butan-1-one;

1-(3-bromo-1-oxa-2,8-diazaspiro[4.5]dec-2-en-8-yl)-4,4,4-trifluorobutan-1-one;

1-(3-ethoxy-1-oxa-2,8-diazaspiro[4.5]dec-2-en-8-yl)-4,4,4-trifluorobutan-1-one;

4,4,4-trifluoro-1-(3-methoxy-1-oxa-2,8-diazaspiro[4.5]dec-2-en-8-yl)butan-1-one;

4,4,4-trifluoro-1-(3-(trifluoromethyl)-1-oxa-2,8-diazaspiro[4.5]dec-2-en-8-yl)butan-1-one;

4,4,4-trifluoro-1-(3-methyl-1-oxa-2,8-diazaspiro[4.5]dec-2-en-8-yl)butan-1-one;

1-(3-ethyl-1-oxa-2,8-diazaspiro[4.5]dec-2-en-8-yl)-4,4,4-trifluorobutan-1-one;

8-(4,4,4-trifluorobutanoyl)-1-oxa-2,8-diazaspiro[4.5]dec-2-ene-3-carbonitrile; and 4,4,4-trifluoro-1-(3-fluoro-1-oxa-2,8-diazaspiro[4.5]dec-2-en-8-yl)butan-1-one.

Terms and Definitions

As used herein, the term "halogen" refers to fluoro, chloro, bromo or iodo. However, more particularly, it is intended to refer to flouro, chloro or bromo.

As used herein, the term "cyano" refers to —CN.

As used herein, the term "$C_{1-6}$ straight alkyl" refers to a straight chain alkyl group having one to six carbon atoms. Therefore, the term "$C_{1-6}$ straight alkyl" includes methyl, ethyl, n-propyl, n-butyl, n-pentyl and n-hexyl.

As used herein, the term "$C_{3-4}$ branched alkyl" refers to a branched alkyl group having three or four carbon atoms. Therefore, the term "$C_{3-4}$ branched alkyl" includes iso-propyl, sec-butyl and iso-butyl.

As used herein, the term "$C_{1-6}$ straight alkoxy" refers to a straight chain alkoxy group having one to three carbon atoms. Therefore, the term "$C_{1-6}$ straight alkoxy" includes methoxy, ethoxy, n-propoxy, n-butoxy, n-pentyloxy and n-hexyloxy.

As used herein, the term "$C_{3-4}$ branched alkoxy" refers to a branched chain alkoxy group having three or four carbon atoms. Therefore, the term "$C_{3-4}$ branched alkoxy" includes iso-propoxy, sec-butoxy and iso-butoxy.

As used herein, the term "methyl substituted by one or more fluoro" refers to a methyl group which is substituted by one, two or three fluorine atoms. Therefore, the term "methyl substituted by one or more fluoro" includes monofluoromethyl ($—CH_2F$), di-fluoromethyl ($—CHF_2$) and trifluoromethyl ($—CF_3$).

As used herein, the term "ethyl substituted by one or more fluoro" refers to an ethyl group which is substituted by one, two, three, four or five fluorine atoms. Therefore, the term "ethyl substituted by one or more fluoro" includes 2-fluoroethyl ($—CH_2CH_2F$), 2,2-difluoroethyl ($—CH_2CHF_2$) and 2,2,2-trifluoroethyl ($—CH_2CF_3$).

As used herein, the term "methoxy substituted by one or more fluoro" refers to a methoxy group wherein the carbon of the methyl group is substituted by one, two or three fluorine atoms. Therefore, the term "methyl substituted by one or more fluoro" includes mono-fluoromethoxy ($—OCH_2F$), di-fluoromethoxy ($—OCHF_2$) and trifluoromethoxy ($—OCF_3$).

As used herein, the term "ethoxy substituted by one or more fluoro" refers to an ethoxy group wherein a carbon of the ethyl group is substituted by one, two, three, four or five fluorine atoms.

Therefore, the term "ethyl substituted by one or more fluoro" includes 2-fluoroethoxy ($—OCH_2CH_2F$), 2,2-difluoroethoxy ($—OCH_2CHF_2$) and 2,2,2-trifluoroethoxy ($—OCH_2CF_3$).

It will be appreciated that a compound of Formula (I) may exist in different tautomeric forms. All possible tautomers are contemplated to be within the scope of the present invention.

The term "compounds of the invention" as used herein means a compound of Formula (I) or a pharmaceutically acceptable salt thereof. The term "a compound of the invention" means any one of the compounds of the invention as defined above.

Furthermore, it will be understood that phrases such as "a compound of Formula (I) or a pharmaceutically acceptable salt thereof" or "compounds of the invention" are intended to encompass the compound of Formula (I), a pharmaceutically acceptable salt or solvate of the compound of Formula (I), or any pharmaceutically acceptable combination of these. Thus by way of non-limiting example used here for illustrative purpose, "a compound of Formula (I) or a pharmaceutically acceptable salt thereof" encompasses a pharmaceutically acceptable salt of a compound of Formula (I) which is present as a solvate, and this phrase also encompasses a mixture of a compound of Formula (I) and a pharmaceutically acceptable salt of a compound of Formula (I).

It is to be understood that references herein to a compound of Formula (I) or a pharmaceutically acceptable salt thereof includes a compound of Formula (I) as a free base or as a pharmaceutically acceptable salt thereof. Thus, in one embodiment, the invention is directed to a compound of Formula (I). In another embodiment, the invention may be directed to a pharmaceutically acceptable salt of a compound of Formula (I).

The term "pharmaceutically acceptable" refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Pharmaceutically acceptable salts include, amongst others, those described in Berge, J. Pharm. Sci., 1977, 66, 1-19, or those listed in P H Stahl and C G Wermuth, editors, Handbook of Pharmaceutical Salts; Properties, Selection and Use, Second Edition Stahl/Wermuth: Wiley-VCH/VHCA, 2011 (see http://www.wiley.com/WileyCDA/WileyTitle/productCd-3906390519.html).

Suitable pharmaceutically acceptable salts can include acid addition salts. Such salts can be formed by reaction with the appropriate acid, optionally in a suitable solvent such as an organic solvent, to give the salt which can be isolated by crystallisation and filtration.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

As used herein, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder.

An appropriate "therapeutically effective amount" will depend upon a number of factors including, for example, the age and weight of the subject, the precise condition requiring treatment and its severity, the nature of the formulation, and the route of administration, and will ultimately be at the discretion of the attendant physician.

Compound Preparation

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention.

Specific compounds of the invention can be prepared according to the experimental procedures disclosed in the Examples section.

The general procedures used to synthesise the compounds of Formula (I) are described in reaction Schemes 1 to 7 below and are illustrated in the Examples.

Preparation of Compounds of Formula (Ia)

(Ia)

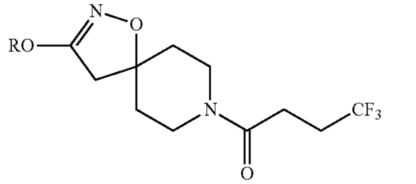

Compounds of Formula (Ia), which are alkoxyspiro compounds of Formula (I), may be prepared according to Scheme 1 (below) by deprotection of Boc protecting group of alkoxyspiro compound of Formula (II) with, for example TFA, and further coupling of the TFA salt amino group with 4,4,4-trifluorobutanoic acid. Intermediate compound Formula (II) can be prepared by reaction of corresponding commercially available alcohols (ROH) with halogenated spiro N-Boc protected compound of Formula (IV), the synthesis of which is described below.

Scheme 1 - Preparation of compounds of Formula (I) where in $R^1$ is $C_{1-6}$ straight alkoxy; $C_{3-4}$ branched alkoxy; methoxy sunstituted by one or more fluoro; or ethoxy substituted by one or more fluoro

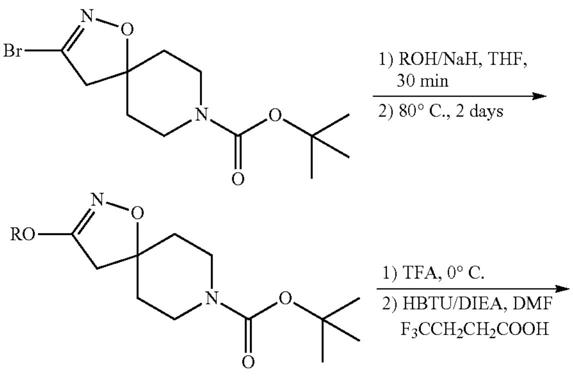

(II)

-continued

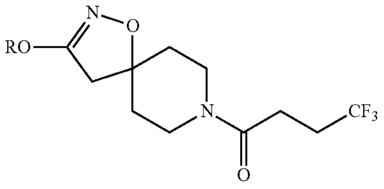

(Ia)

Alternatively, compounds of Formula (Ia) which are alkoxyspiro compounds may be prepared according to Scheme 2 (below) by reaction of the corresponding commercially available alcohols (ROH) with halogenated spiro trifluorobutanamide compound of formula (IIIa) in the presence of a suitable base, such as potassium carbonate.

Scheme 2 - Alternative preparation of compounds of Formula (I) where in $R^1$ is $C_{1-6}$ straight alkoxy; $C_{3-4}$ branched alkoxy; methoxy sunstituted by one or more fluoro; or ethoxy substituted by one or more fluoro

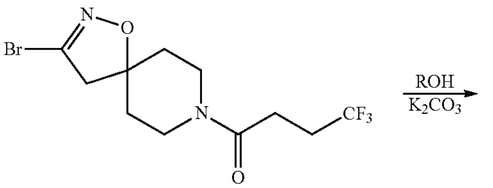

(IIIa)

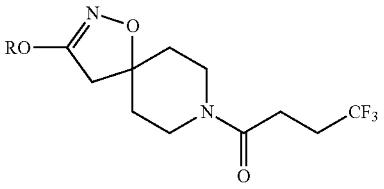

(Ia)

Preparation of Compounds of Formula (Ib)

Compounds of Formula (Ib), which are alkylspiro compounds, may be prepared according to Scheme 3 (below) by coupling of a compound of Formula (IV) with 4,4,4-trifluorobutanoic acid. Compounds of Formula (IV) may be prepared by cyclisation of commercially available tert-butyl 4-methylenepiperidine-1-carboxylate with oxime compounds of Formula (V) and further cleavage of N-Boc protecting group with an acid, such as hydrogen chloride.

Scheme 3 - Preparation of compounds of Formula (I) where in R1 is C1-6 straight alkoxy or C3-4 branched alkyl

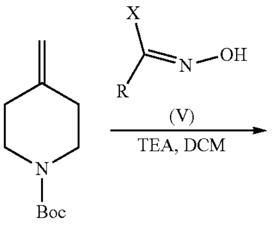

-continued

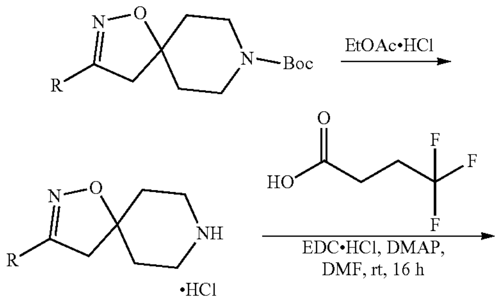

(IV)

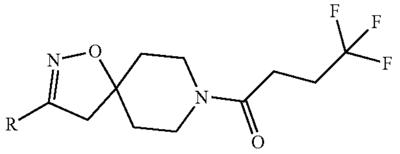

(Ib)

Preparation of Compound of Formula (Ic)

Cyano compound of Formula (Ic) may be prepared by nucleophilic substitution of compound (IIIa) with, for example, sodium cyanide in a suitable solvent such as DMF, in accordance with Scheme 4 (below).

Scheme 4 - Preparation of compounds of Formla (I) wherein $R^1$ is CN

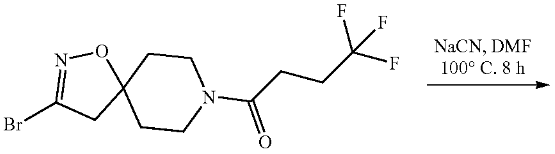

(IIIa)

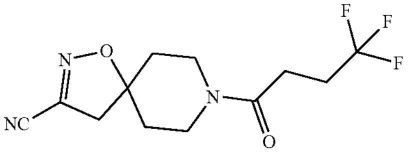

(Ic)

Preparation of Compound of Formula (Id)

Fluorine compound of Formula (Id) may be prepared by halogen substitution of compound (IIIa) with, for example, potassium fluoride in a suitable solvent such as DMSO, in accordance with Scheme 5 (below).

Scheme 5 - Preparation of compounds of Formla (I) wherein $R^1$ is F

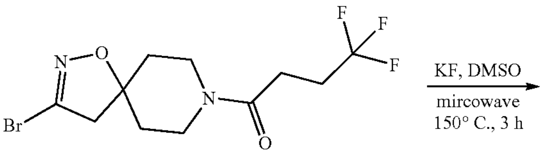

(IIIa)

-continued

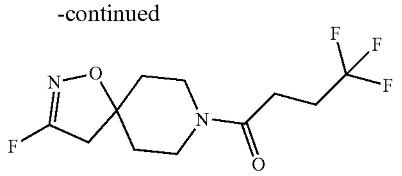

(Ic)

Preparation of Intermediates (IIa) and (V)

Oxime intermediates of Formula (V), may be prepared by halogenation reaction of intermediate compounds of Formula (VI) with N-halogensuccinimide, such as NBS or NCS as shown in Scheme 6 (below). Oxime intermediates of Formula (VI), wherein R is methyl or ethyl may be prepared by reaction of the corresponding aldehyde of Formula (VII) with, for example, hydroxylamine. Alternatively, the trifluoromethyloxime intermediate, wherein R is trifluoromethyl, can be prepared by reaction of 2,2,2-trifluoro-1-methoxy-ethanol with hydroxyl amine.

Scheme 6 - Preparation of intermediate V

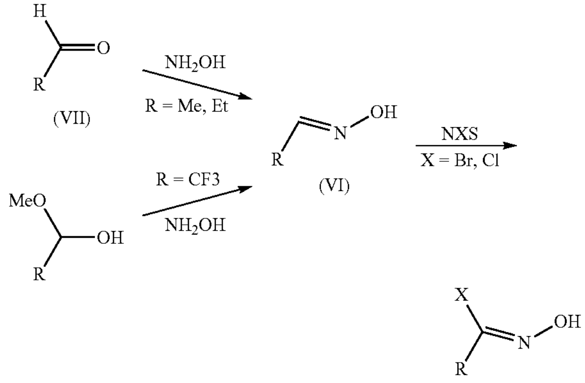

(VII) (VI) (V)

Halogenated spiro N-Boc protected intermediate of Formula (III) may be prepared by reaction of commercially available tert-butyl 4-methylenepiperidine-1-carboxylate and hydroxycarbonimidic dibromide in the presence of, for example, sodium bicarbonate (Scheme 7).

Scheme 7 - Preparation of intermediate III

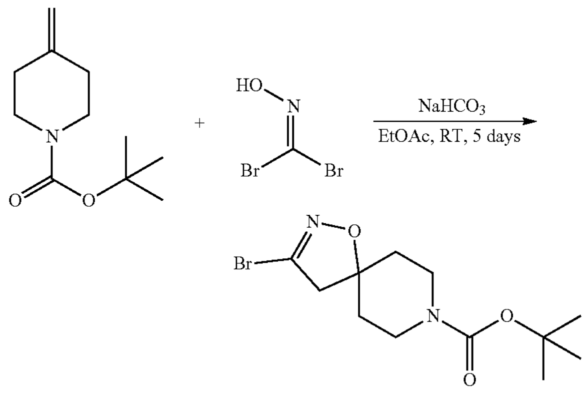

In a similar manner, intermediate (IIIa) may be prepared by reaction of alkene (VIII) with hydroxycarbonimidic dibromide under the same conditions as described above. Intermediate (VIII) can be prepared by coupling reaction of amino hydrochloride intermediate (IX) with 4,4,4-trifluorobutanoic acid under standard conditions. Finally, amino intermediate (IX) may be prepared from commercially available tert-butyl 4-methylenepiperidine-1-carboxylate by treatment with hydrogen chloride. In this regard see Scheme 8 below.

Scheme 8 - Preparation of intermediate IIIa

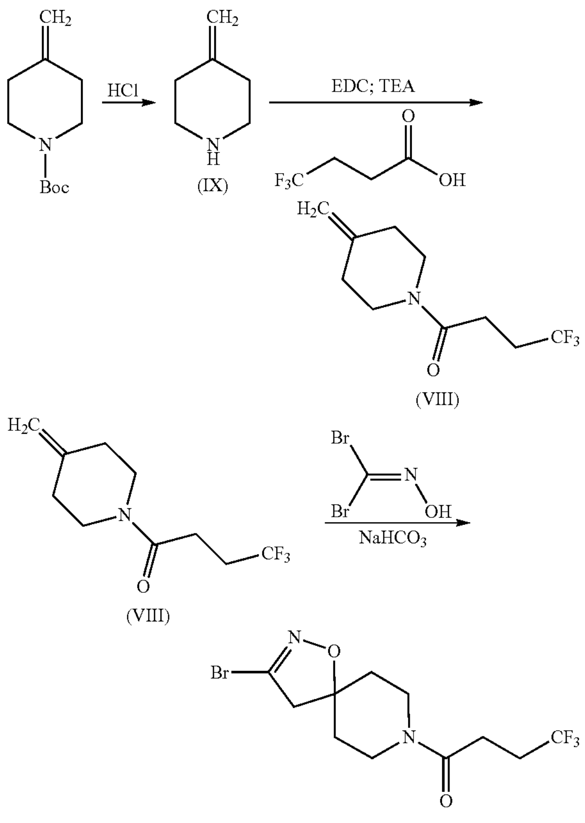

(IX) (VIII) (VIII) (IIIa)

Methods of Use

In one aspect, the invention relates to a compound of Formula (I), or a pharmaceutically acceptable salt thereof, for use in therapy.

In another aspect, the invention relates to a compound of Formula (I), or a pharmaceutically acceptable salt thereof, for use in the treatment of a mycobacterial infection. A mycobacterial infection is one caused by infection with a *mycobacterium.*

The *mycobacterium* may be a member of one of the following groups of *mycobacterium: Mycobacterium tuberculosis* complex (MTC), *Mycobacterium avium* complex (MAC), *Mycobacterium gordonae* clade, *Mycobacterium kansasii* clade, *Mycobacterium chelonae* clade, *Mycobacterium fortuitum* clade, *Mycobacterium parafortuitum* clade or *Mycobacterium vaccae* clade. The *mycobacterium* may also be *Mycobacterium ulcerans* or *Mycobacterium leprae.*

Members of *Mycobacterium tuberculosis* complex (MTC) include *Mycobacterium tuberculosis, Mycobacterium africanum, Mycobacterium bovis, Mycobacterium bovis* BCG, *Mycobacterium canetti, Mycobacterium caprae, Mycobacterium microti* and *Mycobacterium pinnipedii.*

These mycobacteria are causative agents of human and animal tuberculosis. *Mycobacterium tuberculosis* is the major cause of human tuberculosis.

In one embodiment, the *mycobacterium* is a member of the *Mycobacterium tuberculosis* complex (MTC).

In one embodiment, the infection is a *Mycobacterium tuberculosis* infection. In other words, the mycobacterial infection is caused by infection with *Mycobacterium tuberculosis.*

In one embodiment, the *Mycobacterium tuberculosis* is multidrug-resistant. In another embodiment the *Mycobacterium tuberculosis* is resistant to ethionamide.

Members of *Mycobacterium avium* complex (MAC) include *Mycobacterium avium, Mycobacterium avium paratuberculosis, Mycobacterium avium silaticum, Mycobacterium avium hominissuis, Mycobacterium columbiense* and *Mycobacterium indicus pranii.*

Members of *Mycobacterium gordonae* clade include *Mycobacterium asiaticum* and *Mycobacterium gordonae.*

Members of *Mycobacterium kansasii* clade include *Mycobacterium gastri* and *Mycobacterium kansasii.*

Members of *Mycobacterium chelonae* clade include *Mycobacterium abscessus, Mycobacterium bolletii* and *Mycobacterium chelonae.*

Members of *Mycobacterium fortuitum* clade include *Mycobacterium boenickei, Mycobacterium brisbanense, Mycobacterium cosmeticum, Mycobacterium fortuitum, Mycobacterium fortuitum* subspecies *acetamidolyticum, Mycobacterium houstonense, Mycobacterium mageritense, Mycobacterium neworleansense, Mycobacterium peregrinum, Mycobacterium porcinum, Mycobacterium senegalense* and *Mycobacterium septicum.*

Members of *Mycobacterium parafortuitum* clade include *Mycobacterium austroafricanum, Mycobacterium diernhoferi, Mycobacterium frederiksbergense, Mycobacterium hodleri, Mycobacterium neoaurum* and *Mycobacterium parafortuitum.*

Therefore, the mycobacterial infection may be caused by infection with a *mycobacterium* selected from the following: *Mycobacterium tuberculosis, Mycobacterium africanum, Mycobacterium bovis, Mycobacterium bovis* BCG, *Mycobacterium canetti, Mycobacterium caprae, Mycobacterium microti, Mycobacterium pinnipedii, Mycobacterium avium, Mycobacterium avium paratuberculosis, Mycobacterium avium silaticum, Mycobacterium avium hominissuis, Mycobacterium columbiense, Mycobacterium indicus pranii, Mycobacterium asiaticum, Mycobacterium gordonae, Mycobacterium gastri, Mycobacterium kansasii, Mycobacterium abscessus, Mycobacterium bolletii, Mycobacterium chelonae*, include *Mycobacterium boenickei, Mycobacterium brisbanense, Mycobacterium cosmeticum, Mycobacterium fortuitum, Mycobacterium fortuitum* subspecies *acetamidolyticum, Mycobacterium houstonense, Mycobacterium mageritense, Mycobacterium neworleansense, Mycobacterium peregrinum, Mycobacterium porcinum, Mycobacterium senegalense, Mycobacterium septicum, Mycobacterium austroafricanum, Mycobacterium diernhoferi, Mycobacterium frederiksbergense, Mycobacterium hodleri, Mycobacterium neoaurum, Mycobacterium parafortuitum, Mycobacterium ulcerans* and *Mycobacterium leprae.*

In another aspect, the invention relates to a compound of Formula (I), or a pharmaceutically acceptable salt thereof, for use in the treatment of a disease caused by infection with a *mycobacterium*, where the *mycobacterium* is selected from those hereinbefore described.

Diseases caused by infection with a *mycobacterium* include, but are not limited to, tuberculosis (e.g. from *Mycobacterium tuberculosis*), leprosy (e.g. from *Mycobacterium leprae*), Johne's disease (e.g. from *Mycobacterium avium* subspecies *paratuberculosis*), Buruli or Bairnsdale ulcer (e.g. from *Mycobacterium ulceran*), Crohn's disease (e.g. from *Mycobacterium avium* subspecies *paratuberculosis*), pulmonary disease or pulmonary infection, pneumonia, bursa, synovial, tendon sheaths, localized abscess, lymphadenitis, skin and soft tissue infections, Lady Windermere syndrome (e.g. from *Mycobacterium avium* complex (MAC)), MAC lung disease, disseminated *Mycobacterium avium* complex (DMAC), disseminated *Mycobacterium avium* intraceullulare complex (DMAIC), hot-tub lung (e.g. from *Mycobacterium avium* complex), MAC mastitis, MAC pyomyositis, or granuloma disease.

In one embodiment, the disease is tuberculosis. Thus, one aspect of the invention relates to a compound of Formula (I), or a pharmaceutically acceptable salt thereof, for use in the treatment of tuberculosis.

In one embodiment, the invention relates to a method of treatment of a mycobacterial infection in a mammal in need thereof, said treatment comprising administering to said mammal a therapeutically effective amount of a compound of Formula (I), or pharmaceutically acceptable salt thereof. As described herein, a mycobacterial infection is one caused by infection with a *mycobacterium*. The *mycobacterium* is as hereinbefore described.

In one embodiment, the mycobacterial infection is a *Mycobacterium tuberculosis* infection.

In another embodiment, the invention relates to a method of treatment of a disease caused by infection with a *mycobacterium* in a mammal in need thereof, said treatment comprising administering to said mammal a therapeutically effective amount of a compound of Formula (I), or a pharmaceutically acceptable salt thereof.

In one embodiment, the disease is tuberculosis. Therefore, also described herein is a method of treatment of tuberculosis in a mammal in need thereof, said treatment comprising administering to said mammal a therapeutically effective amount of a compound of formula (I), or a pharmaceutically acceptable salt thereof.

In one embodiment, the mammal is a human.

It will be appreciated by those skilled in the art that references herein to treatment refer to the treatment of established conditions. However, compounds of the invention may, depending on the condition, also be useful in the prevention of certain diseases. Thus, in one embodiment, there is provided the treatment or prevention of a disease such as TB. In another embodiment, there is provided the treatment of a disease such as TB. In a further embodiment, there is provided the prevention of a disease such as TB.

In another embodiment, the invention relates to use of a compound of Formula (I), or a pharmaceutically acceptable salt thereof, in the manufacture of a medicament for use in the treatment of a mycobacterial infection or in the treatment of a disease caused by infection with a *mycobacterium.*

Also described herein is the use of a compound of Formula (I), or a pharmaceutically acceptable salt thereof, in the manufacture of a medicament for use in the treatment of tuberculosis.

In one embodiment, a compound of Formula (I) or pharmaceutically acceptable salt thereof, for use in the treatment of TB is co-administered with a thioamide. In a further embodiment, the thioamide is ethionamide. In an alternative embodiment, the thioamide is prothionamide.

Consequently, in one embodiment there is provided a pharmaceutical composition for use in the treatment of TB, wherein said composition comprises (a) a compound of Formula (I); (b) a thioamide, for example ethionamide or prothionamide; and optionally (c) a pharmaceutically acceptable excipient.

In another embodiment, the invention relates to a method of treatment of a mycobacterial infection in a mammal in need thereof, said treatment comprising administering to said mammal a therapeutically effective amount of a compound of Formula (I), or pharmaceutically acceptable salt thereof, in combination with a thioamide, wherein said thioamide may be ethionamide. In an alternative embodiment, the thioamide is prothionamide. As described herein, a mycobacterial infection is one caused by infection with a *mycobacterium*. The *mycobacterium* is as hereinbefore described.

In one embodiment, the mycobacterial infection is a *Mycobacterium tuberculosis* infection.

In another embodiment, the invention relates to a method of treatment of a disease caused by infection with a *mycobacterium* in a mammal in need thereof, said treatment comprising administering to said mammal a therapeutically effective amount of a compound of Formula (I), or a pharmaceutically acceptable salt thereof, in combination with a thioamide, wherein said thioamide may be ethionamide. In an alternative embodiment, the thioamide is prothionamide.

In one embodiment, the disease is tuberculosis. Therefore, also described herein is a method of treatment of tuberculosis in a mammal in need thereof, said treatment comprising administering to said mammal a therapeutically effective amount of a compound of Formula (I), or a pharmaceutically acceptable salt thereof, in combination with a thioamide, wherein said thioamide may be ethionamide. In an alternative embodiment, the thioamide is prothionamide.

In another embodiment, the invention relates to use of a compound of Formula (I), or a pharmaceutically acceptable salt thereof, in combination with a thioamide (for example, ethionamide), in the manufacture of a medicament for use in the treatment of a mycobacterial infection or in the treatment of a disease caused by infection with a *mycobacterium*. In an alternative embodiment, the thioamide is prothionamide.

Also described herein is the use of a compound of Formula (I), or a pharmaceutically acceptable salt thereof, in combination with a thioamide (for example, ethioamide) in the manufacture of a medicament for use in the treatment of tuberculosis. In an alternative embodiment, the thioamide is prothionamide.

In an embodiment, the compound of Formula (I) for use in the above described methods and treatments is 4,4,4-trifluoro-1-(3-(trifluoromethyl)-1-oxa-2,8-diazaspiro[4.5]dec-2-en-8-yl)butan-1-one having the following structure:

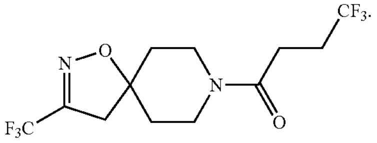 [SMILES: O=C(CCC(F)(F)F)N1CCC2(CC1)CC(C(F)(F)F)=NO2]

Pharmaceutical Compositions

The compounds of Formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of Formula (I), or a pharmaceutically acceptable salt thereof, and a pharmaceutically acceptable excipient.

Pharmaceutical compositions may be administered by any appropriate route, for example by the oral (including buccal or sublingual), rectal, inhaled, intranasal, topical (including buccal, sublingual or transdermal) or parenteral (including subcutaneous, intramuscular, intravenous or intradermal) route. In particular, pharmaceutical compositions of the invention may be administered by oral or intravenous route.

Suitable pharmaceutically acceptable excipients include the following types of excipients: carriers, diluents, fillers, binders, disintegrants, lubricants, glidants, granulating agents, coating agents, wetting agents, solvents, co-solvents, suspending agents, emulsifiers, sweetners, flavouring agents, flavour-masking agents, colouring agents, anti-caking agents, humectants, chelating agents, plasticisers, viscosity increasing agents, antioxidants, preservatives, stabilisers, surfactants and buffering agents.

Suitable methods for formulating compounds of the invention will be familiar to those skilled in the art, which are described in Remington: The Science and Practice of Pharmacy, $21^{st}$ Edition 2006.

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

When the compounds of the invention or pharmaceutically acceptable salts thereof are used in the treatment of tuberculosis, they may be employed alone or in combination with a further therapeutic agent, such as a further anti-mycobacterial agent, for example an anti-tuberculosis agent and/or antiviral agent, including antiretroviral agents.

For example, the present invention relates to compounds of Formula (I) or pharmaceutically acceptable salts thereof, in combination with a further anti-tuberculosis agent. In an embodiment, the combination comprises two, three, four, five, six or seven additional anti-tuberculosis agents. For example, in the treatment of multidrug-resistant tuberculosis, it is common that combinations of four or more drugs are administered to patients. For example, in the treatment of drug-sensitive tuberculosis, it is common that combinations of three or four drugs are administered to patients.

The further anti-tuberculosis agent is an agent in development, approved or recommended for the treatment of tuberculosis and may be selected from isoniazid, rifampin, pyrazinamide, ethambutol, moxifloxacin, rifapentine, clofazimine, ethionamide, prothionamide, isoxyl, thiacetazone, rifabutin, a diarylquinoline such as bedaquiline (TMC207) or TBAJ-587, nitroimidazo-oxazine PA-824, delamanid (OPC-67683), an oxazolidinone such as linezolid, tedizolid, radezolid, sutezolid (PNU-100480), posizolid (AZD-5847) orTBI-223, EMB analogue SQ109, OPC-167832, GSK3036656 (also known as GSK070), GSK2556286, GSK3211830, a benzothiazinone such as BTZ043 or PBTZ169, an azaindole such as TBA-7371, a dinitrobenzamide, or a beta-lactam such as meropenem, faropenem, ertapenem, tebipenem or beta-lactam combinations such as AUGMENTIN (amoxicillin-clavulanate).

In an embodiment, the anti-tuberculosis agent may be selected from isoniazid, rifampin, pyrazinamide, ethambutol, moxifloxacin, rifapentine, clofazimine, ethionamide, prothionamide, isoxyl, thiazetazone, bedaquiline (TMC207), nitroimidazo-oxazine PA-824, delamanid (OPC-67683), an oxazolidinone such as linezolid, tedizolid, radezolid, sutezolid (PNU-100480), or posizolid (AZD-5847), EMB analogue SQ109, OPC-167832, GSK3036656A (also known as GSK070), GSK2556286, GSK3211830 and a benzothiazinone or a dinitrobenzamide.

A combination according to the present invention may further comprise an antiviral agent, including an antiretroviral agents.

Such antiretroviral agents may be selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir and darunavir.

A compound of the invention (i.e. a compound of Formula (I) or pharmaceutically acceptable salt thereof) may be used in combination with an anti-tuberculosis agent that is activatable via the EthA pathway. A person skilled in the art is able to determine if a particular compound is activatable via the EthA pathway, for example, by applying the method described in the following publication: "Activation of the prodrug ethionamide is regulated by mycobacteria" A. R. Baulard et al., Journal of Biological Chemistry, 2000, pages 28326-28331.

More particularly, the anti-tuberculosis agent may be chosen from the thioamide family, such as ethionamide, prothionamide, isoxyl and thiazetazone.

In one embodiment, a compound of the invention (i.e. a compound of Formula (I) or pharmaceutically acceptable salt thereof) is used in combination with ethionamide. In this embodiment, the compounds of the invention (i.e. a compound of Formula (I) or pharmaceutically acceptable salt thereof) have shown to potentiate the activity of ethionamide.

The combinations may conveniently be presented for use in the form of a pharmaceutical composition or formulation. Therefore, also contemplated herein is a pharmaceutical composition comprising (a) a compound of the invention (i.e. a compound of Formula (I) or pharmaceutically acceptable salt thereof), as herein described, together with (b) one or more pharmaceutically acceptable carriers as herein described, and (c) at least one other anti-tuberculosis drug and (d) optionally an antiviral agent including antiretroviral agents.

A compound of the invention (i.e. a compound of Formula (I) or pharmaceutically acceptable salt thereof) and further therapeutic agent may be administered together or separately and, when administered separately, this may occur separately or sequentially in any order (by the same or by different routes of administration). The amount of a compound of the invention (i.e. a compound of Formula (I) or pharmaceutically acceptable salt thereof) and the further therapeutically active agent(s) and the relative timings of administration will be selected in order to achieve the desired combined therapeutic effect.

EXAMPLES

The invention will now be illustrated by way of the following non-limiting examples. While particular embodiments of the invention are described below a skilled person will appreciate that various changes and modifications can be made. References to preparations carried out in a similar manner to, or by the general method of, other preparations, may encompass variations in routine parameters such as time, temperature, workup conditions, minor changes in reagents amounts, etc.

Abbreviations

The following list provides definitions of certain abbreviations and symbols as used herein. It will be appreciated that the list is not exhaustive, but the meaning of those abbreviations and symbols not herein below defined will be readily apparent to those skilled in the art. In describing the invention, chemical elements are identified in accordance with the Periodic Table of the Elements.

ACN Acetonitrile
anh Anhydrous
$CDCl_3$ Deuterated chlorofom
$CD_2Cl_2$ Deuterated dichloromethane
CyHex Cyclohexane
DCM Dichloromethane
DIPEA Diisoproylethylamine
DMAP 4-Dimethylaminopyridine
DMF Dimethylformamide
DMSO-$d_6$ Deuterated dimethylsulfoxide
EDC 1-Ethyl-3-(3-dimethylaminopropyl)carbodiimide
EtOAc Ethyl acetate
Ex. Example
HBTU N,N,N',N'-Tetramethyl-O-(1H-benzotriazol-1-yl) uronium hexafluorophosphate
HPLC High Performance Liquid Chromatography
Int. Intermediate
M Molar
MS Mass spectroscopy
min Minutes
N Normal
NaH Sodium hydride
NMR Nuclear Magnetic Resonance
TFA Trifluoroacetic acid
TEA Triethylamine
THE Tetrahydrofuran
TLC Thin layer chromatography
rt Room temperature
UPLC Ultra Performance Liquid Chromatography Proton nuclear magnetic resonance ($^1H$ NMR) spectra were recorded, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. Mass spectra were obtained using electrospray (ES) ionization techniques. All temperatures are reported in degrees centigrade.

In certain of the following Intermediates and Examples, starting materials are identified by reference to other Intermediate or Example numbers. This does not signify that the actual material from any particular Intermediate or Example was necessarily used in a subsequent step exemplified herein, but is used as a short-hand means of denoting the relevant compound name.

INTERMEDIATES

Intermediate 1: tert-butyl 3-bromo-1-oxa-2,8-diazaspiro[4.5]dec-2-ene-8-carboxylate

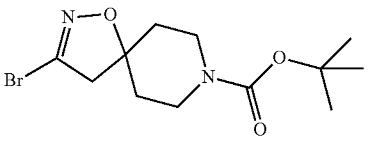 [SMILES: CC(C)(C)OC(=O)N1CCC2(CC1)CC(Br)=NO2]

To a suspension of tert-butyl 4-methylenepiperidine-1-carboxylate (FLUOROCHEM, 2 g, 10.14 mmol) and sodium bicarbonate (8.52 g, 101.38 mmol) in EtOAc (50 mL) was added dibromoformaldoxime (FLUOROCHEM, 5 g, 24.74 mmol). The reaction mixture was stirred for 5 days at rt. Celite was added and the resulting slurry was filtered under vacuum and washed with EtOAc. The solvent was evaporated and the residue was purified by silica chromatography column using a gradient of CyHex/EtOAc as eluents (CyHex/EtOAc 95/5 to 90/10) to yield the title compound (7.29 g, 92%) as a white solid. $^1H$ NMR (300 MHz, $CDCl_3$) δ ppm: 3.72-3.64 (m, 2H), 3.40-3.31 (m, 2H), 2.95 (s, 2H), 1.92-1.84 (m, 2H), 1.72-1.65 (m, 2H), 1.45 (s, 9H). [ES+MS] m/z 319, 321 ($MH^+$).

Intermediate 2: tert-butyl 3-(2,2,2-trifluoroethoxy)-1-oxa-2,8-diazaspiro[4.5]dec-2-ene-8-carboxylate

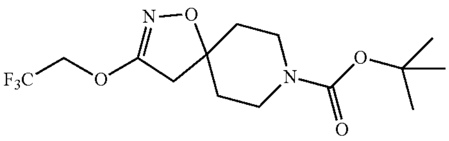 [SMILES: CC(C)(C)OC(=O)N1CCC2(CC1)CC(OCC(F)(F)F)=NO2]

To a solution of 2,2,2-trifluoroethanol (SIGMA-ALDRICH, 282 mg, 2.82 mmol) in 2 mL THE at 0° C. was added NaH (SIGMA-ALDRICH, 112.8 mg, 2.82 mmol) and mixture was stirred for 30 min. Intermediate 1 tert-butyl 3-bromo-1-oxa-2,8-diazaspiro[4.5]dec-2-ene-8-carboxylate (300 mg, 0.94 mmol) was then added at 0° C. and the mixture was stirred at 80° C. for 2 days. The solution was washed with a saturated solution of ammonium chloride and extracted by EtOAc (×2). Organic layers were dried over (anh) $MgSO_4$ and filtered. Solvent was evaporated under vacuum. Residue was purified by silica chromatography column using a gradient of CyHex/EtOAc as eluents (0-20% EtOAc for 30 min and 20% EtOAc for 10 min) to give the title compound (200 mg, 63%). [ES+ MS] m/z 339 ($MH^+$).

Intermediates 3-5 were prepared by methods analogous to that described for Intermediate 2 but replacing the alcohol (2,2,2-trifluoroethanol) with that indicated in Table 1. Products were purified by silica chromatography column using a gradient of CyHex/EtOAc as eluents (0-10% EtOAc for 30 min and 10% EtOAc for 10 min).

TABLE 1

| Int. | Structure | Starting material | Physical data |
|---|---|---|---|
| 3 | 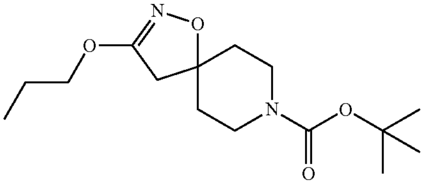 [SMILES: CCCOC1=NOC2(CCN(C(=O)OC(C)(C)C)CC2)C1] | 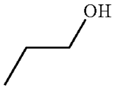 SIGMA-ALDRICH | [ES+ MS] m/z 299 ($MH^+$). |
| 4 | 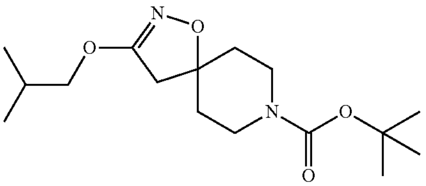 [SMILES: CC(C)COC1=NOC2(CCN(C(=O)OC(C)(C)C)CC2)C1] | 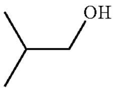 SIGMA-ALDRICH | [ES+ MS] m/z 313 ($MH^+$). |
| 5 | 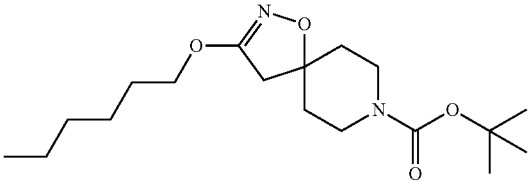 [SMILES: CCCCCCOC1=NOC2(CCN(C(=O)OC(C)(C)C)CC2)C1] | 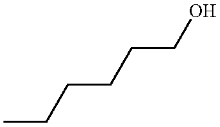 ACROS | [ES+ MS] m/z 341 ($MH^+$). |

Intermediate 6: 4-methylenepiperidine hydrochloride

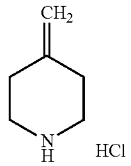

To a solution of tert-butyl 4-methylenepiperidine-1-carboxylate (APOLLO, 10 g, 50.7 mmol) in dioxane (130 mL) at 0° C., a solution of HCl 4M in dioxane (ALFA-AESAR, 130 mL, 507 mmol, 10 eq) was added and the mixture was stirred at rt overnight. Monitoring by UPLC and TLC showed the reaction was completed. The solvent was removed under vacuum to afford the desired compound 4-methylidenepiperidine hydrochloride which was used in the next step without further purification (7.6 g, 100%). $^1$H NMR (400 MHz, DMSO-$d_6$) δ ppm: 9.19 (br s, 2H), 4.86 (s, 2H), 3.06 (t, J=6.0 Hz, 4H), 2.41 (t, J=6.0 Hz, 4H).

Intermediate 7:4,4,4-trifluoro-1-(4-methylenepiperidin-1-yl)butan-1-one

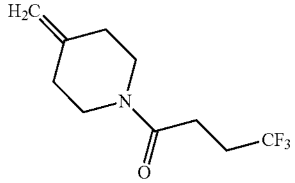

A solution of EDC.HCl (ALFA-AESAR, 19.4 g, 101.3 mmol), TEA (ALFA-AESAR, 28 mL, 202.5 mmol) and 4,4,4-trifluorobutyric acid (ALFA-AESAR, 14.4 g, 101.3 mmol) in DCM (200 mL) was stirred at rt for 10 min, then intermediate 6 (6.77 g, 50.6 mmol) was added and the mixture was stirred at rt overnight. The mixture was then washed with water, the 2 phases were separated and the aqueous one was further extracted with DCM. The collected organic layer was dried over (anh) $Na_2SO_4$, filtered and evaporated. The crude so obtained was purified by flash chromatography (Si SNAP 340, CyHex/EtOAc from 9/1 to 6/4) to give the desired product (10.34 g, 92%) as a pale yellow oil. $^1$H NMR (400 MHz, $CDCl_3$) δ ppm: 4.83 (s, 2H), 3.70-3.59 (m, 2H), 3.51-3.44 (m, 2H), 2.65-2.47 (m, 4H), 2.30-2.21 (m, 4H). [ES+ MS] m/z 222 ($MH^+$).

Intermediate 8: 2,2,2-trifluoroacetaldehyde oxime

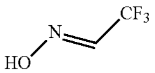

To a stirred solution of 2,2,2-trifluoro-1-methoxyethanol (ALFA-AESAR, 20 g, 153.8 mmol) and hydroxylamine hydrochloride (AVRA, 12.8 g, 184.5 mmol) in methanol (30 mL) was added water (70 mL) at 0° C., followed by the slow addition of a solution of 50% sodium hydroxide (FINAR, 36 mL) at 0° C. The reaction mixture temperature was raised to 26° C. and stirred for 16 h at the same temperature. Reaction was monitored by TLC. On completion of the reaction, n-hexane (250 mL) was added to the reaction mixture and the layers were separated. The aqueous layer was acidified (pH=3) with 6M HCl, then was extracted with diethyl ether (3×500 mL). The organic layer was washed with brine, dried over (anh) $Na_2SO_4$, filtered and concentrated under reduced pressure to afford the titled compound as a colorless liquid (18 g, crude). $^1$H NMR (400 MHz, $CDCl_3$) δ ppm: 9.11 (br s, 1H), 7.54-7.46 (m, 1H).

Intermediate 9: 2,2,2-trifluoro-N-hydroxyacetimidoyl bromide

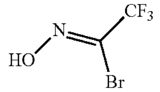

To a stirred solution of Intermediate 8 (18 g, 159.2 mmol) in DMF (90 mL) was added a solution of N-bromosuccinimide (AVRA, 31.1 g, 175.2 mmol) in DMF (90 mL) at 0° C. The reaction mixture was stirred at 26° C. for 3 h. Reaction was monitored by TLC. On completion of the reaction, the reaction mixture was poured into ice water (300 mL) and extracted with diethyl ether (3×400 mL). The organic layer was washed with brine (300 mL), dried over (anh) $Na_2SO_4$, filtered and concentrated under reduced pressure to afford the titled compound (25 g, crude) as a brown oil. $^1$H NMR (400 MHz, $CDCl_3$) δ ppm: 11.55 (br s, 1H).

Intermediate 10: propionaldehyde oxime

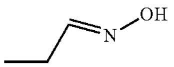

To a stirred solution of propionaldehyde (ALFA-AESAR, 2 g, 34.43 mmol) and $K_2CO_3$ (CHEMLABS, 9.36 g, 68.87 mmol) in DCM (30 mL), hydroxylamine hydrochloride (AVRA, 2.86 g, 41.32 mmol) was added the resultant reaction mixture was stirred for 16 h at 26° C. Reaction was monitored by TLC. On completion the reaction mixture was diluted with water (200 mL) and extracted with DCM (2×50 mL). Combined organic layers were washed with brine solution (50 mL), dried over (anh) $Na_2SO_4$ filtered and concentrated under reduced pressure to afforded tittle compound (1.0 g) as a white solid. The crude compound was used for the next step without any further purification. $^1$H NMR (400 MHz, $CDCl_3$): δ 8.50 (br s, 1H), 6.70 (t, J=5.4 Hz, 1H), 2.26-2.22 (m, 2H), 1.14-1.09 (m, 3H).

Intermediate 11: N-hydroxypropionimidoyl chloride

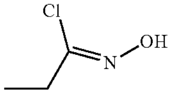

To a stirred solution of Intermediate 10 (1 g, 13.681 mmol) in DMF (10 mL), N-chlorosuccinimide (AVRA, 2.19 g, 16.41 mmol) was added lot wise at 26° C., the reaction mixture was stirred for 30 min at 26° C. Reaction was monitored by TLC. On completion the reaction mixture was diluted with water (100 mL) and extracted with EtOAc (2×50 mL), combined organic layers were washed with brine solution (50 mL), dried over (anh) $Na_2SO_4$, filtered and concentrated under reduced pressure to afford the titled compound as a colorless liquid (1.0 g, 68.4%). $^1$H NMR (400 MHz, $CDCl_3$) δ ppm: 8.32 (br s, 1H), 2.53 (q, J=7.4 Hz, 2H), 1.21 (t, J=7.4 Hz, 3H).

Intermediate 12: N-hydroxyacetimidoyl chloride

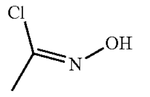

To the solution of (E)-acetaldehyde oxime (TCI, 1 g, 16.949 mmol) in DMF (10 mL) was added N-chlorosuccinimide (AVRA, 2.9 g, 22.03 mmol) in portionwise at 0° C. The reaction mixture temperature was raised to 26° C. for 3 h at the same temperature. Reaction was monitored by TLC. On completion of the reaction, the reaction mixture was diluted with ice water (100 mL) and extracted with diethyl ether (2×300 mL). The organic layer was washed with brine (200 mL), dried over (anh) $Na_2SO_4$, filtered and the filtrate was concentrated under reduced pressure to afford the titled compound (1.2 g, crude) as a colorless liquid. $^1$H NMR (400 MHz, $CDCl_3$) δ ppm: 8.48 (br s, 1H), 2.27 (s, 3H).

Intermediate 13: tert-butyl 3-(trifluoromethyl)-1-oxa-2,8-diazaspiro[4.5]dec-2-ene-8-carboxylate

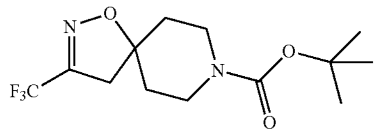 [SMILES: CC(C)(C)OC(=O)N1CCC2(CC1)CC(C(F)(F)F)=NO2]

To a stirred solution of Intermediate 9 (6 g, 30.41 mmol) in DCM (60 mL) was added potassium bicarbonate (ALFA-AESAR, 6.09 g, 60.83 mmol) in portion wise at 0° C. Followed by the addition of tert-butyl 4-methylenecyclohexanecarboxylate (OAKWOOD, 5.86 g, 30.415 mmol) dropwise at 0° C. The reaction mixture was stirred at 26° C. for 16 h. Reaction was monitored by TLC. On completion, the reaction mixture was poured into water (200 mL) and extracted with EtOAc (3×250 mL). The organic layer was washed with brine (200 mL) and dried over (anh) $Na_2SO_4$, then filtered and concentrated under reduced pressure. The crude was purified by column chromatography (silica gel 100-200 mesh), eluted with 0-10% EtOAc in petroleum ether. The pure fractions were collected and concentrated under reduced pressure to afford the titled compound (6.5 g, 56%) as a light yellow liquid. $^1$H NMR (400 MHz, $CDCl_3$) δ ppm: 3.80-3.63 (m, 2H), 3.42-3.35 (m, 2H), 2.91 (q, J=1.5 Hz, 2H), 1.94-1.89 (m, 2H), 1.77-1.67 (m, 2H), 1.47 (s, 9H). [ES- MS] m/z 307 (M-H).

Intermediates 14 and 15: were prepared by methods analogous to that described for Intermediate 13 but replacing Intermediate 9 with that indicated in Table 2, and also changing potassium bicarbonate to TEA.

TABLE 2

| Int. | Structure | Starting material | Physical data |
|---|---|---|---|
| °14 | 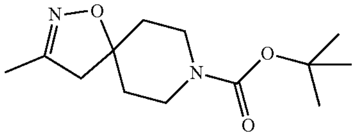 [SMILES: CC1=NOC2(CCN(C(=O)OC(C)(C)C)CC2)C1] | 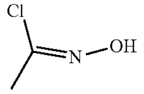 Intermediate 12 | $^1$H NMR (400 MHz, $CDCl_3$) δ ppm: 3.73-3.60 (m, 2H), 3.44-3.27 (m, 2H), 2.67 (s, 2H), 1.98 (s, 3H), 1.85-1.77 (m, 2H), 1.68-1.58 (m, 2H), 1.46 (s, 9H). [ES + MS] m/z 255 (MH$^+$). |
| 15 | 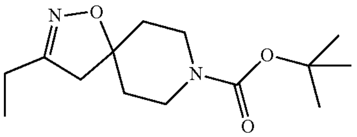 [SMILES: CCC1=NOC2(CCN(C(=O)OC(C)(C)C)CC2)C1] | 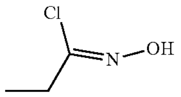 Intermediate 11 | $^1$H NMR (400 MHz, $CDCl_3$) δ ppm: 3.77-3.60 (m, 2H), 3.41-3.34 (m, 2H), 2.67 (s, 2H), 2.35 (q, J = 7.5 Hz, 2H), 1.84-1.79 (m, 2H), 1.67-1.61 (m, 2H), 1.46 (s, 9H), 1.17 (t, J = 7.6 Hz, 3H). |

Intermediate 16: 3-(trifluoromethyl)-1-oxa-2,8-diazaspiro[4.5]dec-2-ene hydrochloride

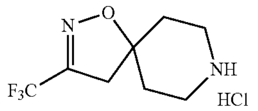 [SMILES: FC(F)(F)C1=NOC2(CCNCC2)C1 ; Cl]

To a stirred solution of Intermediate 13 (3 g, 9.73 mmol) in EtOAc (30 mL) was added 4M HCl in EtOAc (SYMAX, 30 mL) dropwise at 0° C. The reaction mixture was stirred at 260° C. for 2 h. Reaction was monitored by TLC. On completion, the reaction mixture was concentrated under reduced pressure. The residue was washed with diethyl ether (150 mL) and dried to afford the titled compound (2.21 g, crude) as an off-white solid. $^1$H NMR (400 MHz, DMSO-$d_6$) δ ppm: 9.42 (br s, 2H), 3.28 (s, 2H), 3.20-3.04 (n, 4H), 2.14-2.00 (n, 4H). [ES+ MS] m/z 209 (MH$^+$).

Intermediates 17 and 18 were prepared by methods analogous to that described for Intermediate 16 but replacing Intermediate 13 with that indicated in Table 3.

TABLE 3

| Int. | Structure | Starting material | Physical data |
|---|---|---|---|
| 17 | 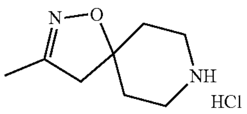 | Intermediate 14 | $^1$H NMR (400 MHz, DMSO-$d_6$) δ ppm: 9.12 (br s, 2H), 3.08-3.01 (m, 4H), 2.84 (s, 2H), 1.88-1.80 (m, 7H). [ES + MS] m/z 155 ($MH^+$). |
| 18 | 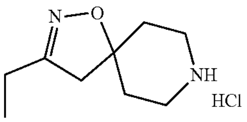 | Intermediate 15 | $^1$H NMR (400 MHz, DMSO-$d_6$) δ ppm: 9.00 (br s, 2H), 3.20-3-10 (m, 4H), 2.85 (s, 2H), 2.28 (q, J = 7.5 Hz, 2H), 1.93-1.81 (m, 4H), 1.06 (t, J = 7.5 Hz, 3H). |

EXAMPLES

Example 1:4,4,4-trifluoro-1-[3-(2,2,2-trifluoroethoxy)-1-oxa-2,8-diazaspiro[4.5]dec-2-en-8-yl]butan-1-one

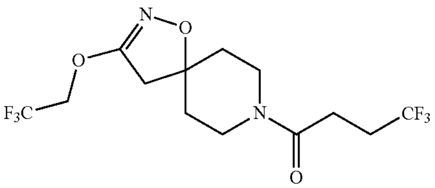 [SMILES: O=C(CCC(F)(F)F)N1CCC2(CC1)CC(OCC(F)(F)F)=NO2]

Intermediate 2 (200 mg, 0.59 mmol) was dissolved in 2 mL of DCM and TFA (2 mL) was added dropwise at 0° C. The mixture was stirred for 10 min at 0° C. A saturated solution of sodium bicarbonate was added to the reaction mixture and the product was extracted with EtOAc. The organic layer was dried over (anh) $MgSO_4$ and filtered then concentrated to dryness to give a yellow residue.

To a solution of DIPEA (ALFA-AESAR, 0.3 ml, 1.76 mmol) in DMF (5 mL) under argon at 0° C., was added HBTU (SIGMA-ALDRICH, 669 mg, 1.76 mmol) and 4,4,4-trifluorobutanoic acid (ALFA-AESAR, 125 mg, 0.88 mmol). The above residue was then added and the mixture was stirred under argon at rt overnight. The DMF was then removed under vacuum. The residue was purified by HPLC (isocratic gradient, ACN/$H_2O$ ammonium formate pH 3.8: 36/64) to yield the title compound (137 mg, 64%). $^1$H NMR (300 MHz, $CD_2Cl_2$) δ ppm: 4.54 (q, J=8.3 Hz, 2H), 4.13-4.05 (m, 1H), 3.66-3.45 (m, 2H), 3.35-3.26 (m, 1H), 2.87 (s, 2H), 2.68-2.37 (m, 4H), 2.10-1.84 (m, 2H), 1.78-1.66 (m, 2H). [ES+ MS] m/z 363 ($MH^+$).

Examples 2-4 were prepared by methods analogous to that described for Example 1, replacing Intermediate 2 with those indicated in Table 4. Modifications in the purification step are also indicated.

TABLE 4

| Ex. | Structure | Starting material | Physical data |
|---|---|---|---|
| 2 | 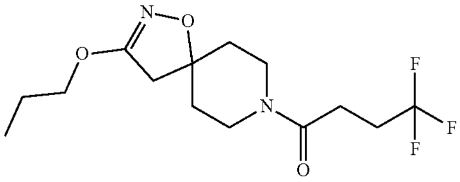<br>4,4,4-trifluoro-1-(3-propoxy-1-oxa-2,8-diazaspiro[4.5]dec-2-en-8-yl)butan-1-one<br>see footnote a | Intermediate 3<br>0.51 mmol | $^1$H NMR (300 MHz, $CD_2Cl_2$) δ ppm: 4.07 (t, 3H, J = 6.6 Hz), 3.64-3.42 (m, 2H), 3.36-3.27 (m, 1H), 2.83-2.70 (m, 2H), 2.68-2.39 (m, 4H), 2.01-1.86 (m, 2H), 1.80-1.56 (m, 4H), 0.99 (t, 3H, J = 7.4 Hz). ES + MS] m/z 323 ($MH^+$). |
| 3 | 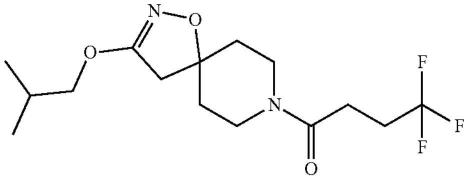<br>4,4,4-trifluoro-1-(3-isobutoxy-1-oxa-2,8-diazaspiro[4.5]dec-2-en-8-yl)butan-1-one<br>see footnote b | Intermediate 4<br>0.67 mmol | $^1$H NMR (300 MHz, $CD_2Cl_2$) δ ppm: 4.10-4.02 (m, 1H), 3.89 (d, J = 6.6 Hz, 2H), 3.59-3.46 (m, 2H), 3.36-3.27 (m, 1H), 2.77 (s, 2H), 2.67-2.37 (m, 4H), 2.12-1.84 (m, 3H), 1.74-1.64 (m, 2H), 0.97 (d, 6H). [ES + MS] m/z 337 ($MH^+$). |

TABLE 4-continued

| Ex. | Structure | Starting material | Physical data |
|---|---|---|---|
| 4 | 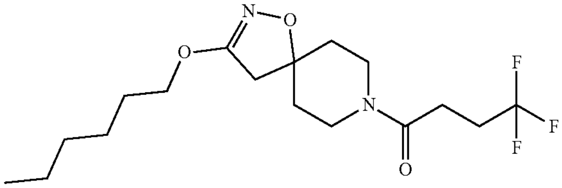 4,4,4-trifluoro-1-(3-hexyloxy-1-oxa-2,8-diazaspiro[4.5]dec-2-en-8-yl)butan-1-one see footnote c | Intermediate 5 0.77 mmol | $^1$H NMR (300 MHz, $CD_2Cl_2$) δ ppm: 4.26-3.95 (m, 3H), 3.59-3.41 (m, 2H), 3.36-3.27 (m, 1H), 2.76 (s, 2H), 2.65-2.35 (m, 4H), 2.04-1.80 (m, 2H), 1.77-1.57 (m, 4H), 1.47-1.18 (m, 6H), 0.98-0.82 (m, 3H). [ES + MS] m/z 365 ($MH^+$). |

a purification by HPLC (pH 3.8, isocratic gradient, ACN/$H_2O$ ammonium formate: 33/67)
b purification by HPLC (pH 3.8, isocratic gradient, ACN/$H_2O$ ammonium formate: 39/61)
c purification by HPLC (pH 3.8, isocratic gradient, ACN/$H_2O$ ammonium formate: 54/46)

Example 5 and Intermediate 19: 1-(3-bromo-1-oxa-2,8-diazaspiro[4.5]dec-2-en-8-yl)-4,4,4-trifluorobutan-1-one

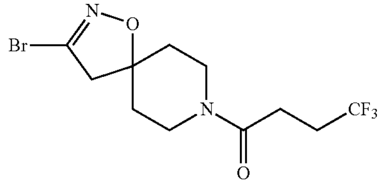 [SMILES: O=C(CCC(F)(F)F)N1CCC2(CC1)CC(Br)=NO2]

To a suspension of Intermediate 7 (9.3 g, 42 mmol) and sodium bicarbonate (ALFA-AESAR, 35.3 g, 420 mmol) in EtOAc (300 ml), dibromoformaldoxime (COMBI-BLOCKS, 10.2 g, 50 mmol) was added and the reaction mixture was stirred at rt for 2 days. Then celite was added and the resulting slurry was filtered under vacuum and washed with EtOAc, the solvent was evaporated and the residue (about 20 g) was purified by flash chromatography (Si SNAP 340, CyHex/EtOAc from 8/2 to 1/1) to give the titled compound (12.23 g, 85%) as a colourless oil. $^1$H NMR (400 MHz, $CDCl_3$) δ ppm: 4.32-4.20 (m, 1H), 3.69-3.60 (m, 1H), 3.59-3.47 (m, 1H), 3.31-3.20 (m, 1H), 3.00 (s, 2H), 2.67-2.43 (m, 4H), 2.07-1.96 (m, 2H), 1.78-1.68 (m, 2H). [ES+ MS] m/z 343, 345 ($MH^+$).

Example 6: 1-(3-ethoxy-1-oxa-2,8-diazaspiro[4.5]dec-2-en-8-yl)-4,4,4-trifluorobutan-1-one

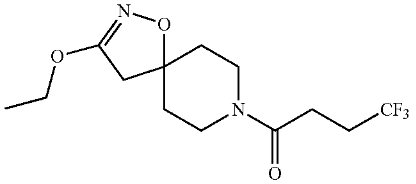 [SMILES: CCOC1=NOC2(CCN(C(=O)CCC(F)(F)F)CC2)C1]

To a stirred solution of Intermediate 19 (0.100 g, 0.29 mmol) in EtOH (4 mL) solid potassium carbonate (ALFA-AESAR, 0.101 g, 0.73 mmol) was added and the resulting suspension was vigorously stirred at 70° C. in a sealed vial for 20 h. UPLC check showed still presence of starting material. To the reaction mixture was then added $K_3PO_4$ (ALFA-AESAR, 0.168 g, 0.73 mmol) and the heating at 70° C. prolonged for 4 h until consumption of the starting material. The suspension was filtered and the filtrate evaporated to give crude material which was submitted to purification by semipreparative LCMS to afford titled compound (0.0427 g, 47%) as a pale yellow solid. $^1$H NMR (400 MHz, DMSO-$d_6$) δ ppm: 4.08 (q, J=7.03 Hz, 2H), 3.65-3.55 (m, 1H), 3.50-3.37 (m, 3H), 2.84 (s, 2H), 2.65-2.56 (m, 2H), 2.49-2.40 (m, 2H), 1.78-1.56 (m, 4H), 1.27 (t, J=7.03 Hz, 3H). [ES+ MS] m/z 309 ($MH^+$).

Example 7: 4,4,4-trifluoro-1-(3-methoxy-1-oxa-2,8-diazaspiro[4.5]dec-2-en-8-yl)butan-1-one

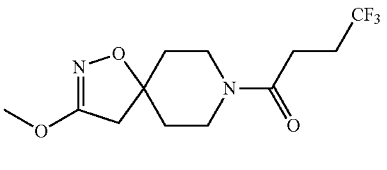 [SMILES: COC1=NOC2(CCN(C(=O)CCC(F)(F)F)CC2)C1]

To a stirred solution of Intermediate 19 (1 g, 2.914 mmol) in Methanol (10 mL) was added sodium methoxide (AVRA, 786 mg, 14.5 mmol) portion wise at 0° C. The reaction mixture was heated to 70° C. for 16 h. Reaction was monitored by TLC. On completion of the reaction, the reaction mixture was quenched with water (100 mL) and extracted with EtOAc (3×200 mL). The organic layer was washed with brine (200 mL), dried over (anh) $Na_2SO_4$, filtered and evaporated under reduced pressure. The crude was purified by column chromatography (silica gel 100-200 mesh), eluted with 0-30% EtOAc in petroleum ether. The pure fractions were collected and concentrated under reduced pressure to afford the titled compound (800 mg, 93%) as an off white solid. $^1$H NMR (400 MHz, $CDCl_3$) δ ppm: 4.24-4.17 (m, 1H), 3.86 (s, 3H), 3.63-3.49 (m, 2H), 3.30-3.21 (m, 1H), 2.75 (s, 2H), 2.62-2.44 (m, 4H), 2.08-1.95 (m, 2H), 1.71-1.61 (m, 2H). [ES+ MS] m/z 295 ($MH^+$).

Example 8: 4,4,4-trifluoro-1-(3-(trifluoromethyl)-1-oxa-2,8-diazaspiro[4.5]dec-2-en-8-yl)butan-1-one

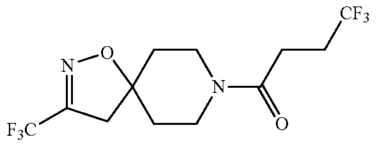

To a stirred solution of Intermediate 16 (2.2 g, 9.016 mmol) and 4,4,4-trifluorobutanoic acid (OAKWOOD, 1.53 g, 10.819 mmol) in DMF (25 mL) were added EDC.HCl (SILVERY, 4.3 g, 22.54 mmol) and DMAP (AVRA, 3.2 g, 27.04 mmol) at 0° C. The reaction mixture was stirred at 26° C. for 16 h. Reaction was monitored by TLC. On completion, the reaction mixture was poured into ice cold water (200 mL) and extracted with EtOAc (3×250 mL). The organic layer was washed with brine (200 mL), dried over (anh) $Na_2SO_4$, filtered and the filtrate was concentrated under reduced pressure. The crude (3.2 g) was purified by column chromatography (silica gel 100-200 mesh), eluted with 0-20% EtOAc in petroleum ether. The pure fractions were collected and concentrated under reduced pressure to afford titled compound (1.7 g, 56%) as a white solid. $^1H$ NMR (400 MHz, $CDCl_3$) δ ppm: 4.33-4.25 (m, 1H), 3.74-3.62 (m, 1H), 3.60-3.49 (m, 1H), 3.33-3.21 (m, 1H), 2.94 (s, 2H), 2.64-2.45 (m, 4H), 2.07-1.94 (m, 2H), 1.80-1.68 (m, 2H). [ES+ MS] m/z 333 ($MH^+$).

Examples 9 and 10 were prepared by methods analogous to that described for Example 8, replacing intermediate 16 with those indicated in Table 5.

Example 11: 8-(4,4,4-trifluorobutanoyl)-1-oxa-2,8-diazaspiro[4.5]dec-2-ene-3-carbonitrile

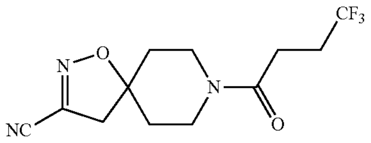 [SMILES: N#CC1=NOC2(CCN(C(=O)CCC(F)(F)F)CC2)C1]

To a stirred solution of Intermediate 1 (5.5 g, 17.231 mmol) in EtOAc (50 mL) was added 4M HCl in EtOAc (SYMAX, 50 mL) at 0° C. Then the reaction mixture was stirred at rt for 3 h. Reaction was monitored by TLC. On completion, the reaction mixture was concentrated under reduced pressure. The residue was triturated with diethyl ether (3×20 mL) and the solid was dried to afford a mixture (4.0 g, rude) 3-chloro-1-oxa-2,8-diazaspiro[4.5]dec-2-ene hydrochloride (mayor, [ES+ MS] m/z 175 ($MH^+$)) and 3-bromo-1-oxa-2,8-diazaspiro[4.5]dec-2-ene hydrochloride (minor, [ES+ MS] m/z 219, 221 ($MH^+$)) as a pale yellow solid.

To a stirred solution of this mixture (500 mg) and 4,4,4-trifluorobutanoic acid (MATRIX, 500 mg, 3.554 mmol) in DMF (10 mL) was added DMAP (AVRA, 860 mg, 4.109 mmol) and EDC.HCl (ASHVARSHA, 1.13 g, 5.92 mmol) at 0° C. The reaction mixture was stirred at rt for 16 h. Reaction was monitored by TLC. On completion, the reaction mixture was poured into ice cold water (50 mL) and extracted with EtOAc (2×50 mL). The organic layer was washed with 1N HCl (50 mL) and brine (100 mL), dried over (anh) $Na_2SO_4$, filtered and the filtrate was evaporated under reduced pres-

TABLE 5

| Ex. | Structure | Intermediate | Physical data |
|---|---|---|---|
| 9 | 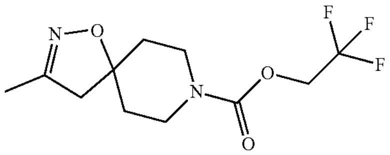 4,4,4-trifluoro-1-(3-methyl-1-oxa-2,8-diazaspiro[4.5]dec-2-en-8-yl)butan-1-one | 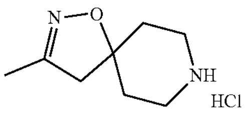 1.83 mmol Intermediate 17 | $^1H$ NMR (400 MHz, $CDCl_3$) δ ppm: 4.26-4.21 (m, 1H), 3.68-3.46 (m, 2H), 3.26-3.21 (m, 1H), 2.70 (s, 2H), 2.64-2.42 (m, 4H), 1.99 (s, 3H), 1.95-1.82 (m, 2H), 1.70-1.58 (m, 2H). [ES + MS] m/z 279 ($MH^+$). |
| 10 | 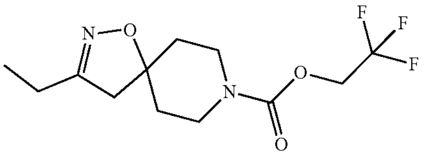 1-(3-ethyl-1-oxa-2,8-diazaspiro[4.5]dec-2-en-8-yl)-4,4,4-trifluorobutan-1-one | 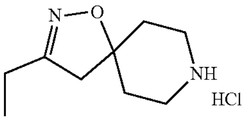 2.1 mmol Intermediate 18 | $^1H$ NMR (400 MHz, $CDCl_3$) δ ppm: 4.26-4.21 (m, 1H), 3.67-3.45 (m, 2H), 3.30-3.21 (m, 1H), 2.69 (s, 2H), 2.63-2.43 (m, 4H), 2.36 (q, J = 7.5 Hz, 2H), 1.97-1.81 (m, 2H), 1.70-1.58 (m, 2H), 1.17 (t, J = 7.6 Hz, 3H). [ES + MS] m/z 293 ($MH^+$). |

sure to afford 600 mg of the following mixture of compounds 1-(3-chloro-1-oxa-2,8-diazaspiro[4.5]dec-2-en-8-yl)-4,4,4-trifluorobutan-1-one and 1-(3-bromo-1-oxa-2,8-diazaspiro[4.5]dec-2-en-8-yl)-4,4,4-trifluorobutan-1-one as a brown colour thick liquid.

To a solution of previous mixture of compounds (200 mg) in DMF (5 mL) was added sodium cyanide (ASHVARSHA, 65 mg, 1.342 mmol) at 26° C. The reaction mixture was heated to 100° C. and stirred for 8 h at the same temperature. The progress of the reaction was monitored by TLC. On completion of the reaction, the reaction mixture was quenched with ice cold water (5 mL) and extracted with EtOAc (2×50 mL). The organic layer was washed with brine (2×50 mL), dried over (anh) $Na_2SO_4$, filtered and the filtrate was concentrated under reduced pressure. The crude was purified by column chromatography (silicagel 100-200 mesh), eluted with 80% EtOAc in petroleum ether. The pure fractions were collected and concentrated under reduced pressure to afford titled compound (150 mg, 78%) as an off-white solid. 1H NMR (400 MHz, $CDCl_3$) δ ppm: 4.35-4.25 (m, 1H), 3.75-3.63 (m, 1H), 3.59-3.49 (m, 1H), 3.32-3.21 (m, 1H), 2.96 (s, 2H), 2.64-2.43 (m, 4H), 2.05-1.92 (m, 2H), 1.80-1.68 (m, 2H). [ES+ MS] m/z 290 (MH$^+$).

Example 12:4,4,4-trifluoro-1-(3-fluoro-1-oxa-2,8-diazaspiro[4.5]dec-2-en-8-yl)butan-1-one

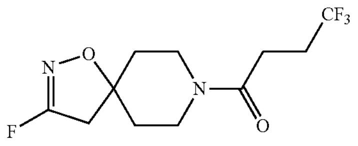 [SMILES: O=C(CCC(F)(F)F)N1CCC2(CC1)CC(F)=NO2]

To a mixture of the same intermediates as Example 11 (1-(3-chloro-1-oxa-2,8-diazaspiro[4.5]dec-2-en-8-yl)-4,4,4-trifluorobutan-1-one and 1-(3-bromo-1-oxa-2,8-diazaspiro[4.5]dec-2-en-8-yl)-4,4,4-trifluorobutan-1-one) (3 g) in DMSO (20 mL) was added potassium fluoride (COMBI-BLOCKS, 1.7 g, 30.131 mmol) portionwise at 26° C. The reaction mixture was heated to 150° C. and stirred for 3 h under microwave condictions. The progress of the reaction was monitored by TLC. On completion of the reaction, the reaction mixture was diluted with water (200 mL) and extracted with EtOAc (2×150 mL). The organic layer was washed with brine (150 mL), dried over (anh) $Na_2SO_4$, filtered and the filtrate was concentrated under reduced pressure. The crude was purified by preparative HPLC (Kromosil column) gradient 16 min from 0% to 100% ACN/$H_2O$ (0.2% formic acid). The pure fractions were collected and the solvent was removed under lyophilization to afford titled compound (11 mg, 0.4%) as a pale yellow gum. 1H NMR (400 MHz, DMSO-$d_6$) δ ppm: 3.61-3.41 (m, 4H), 3.14 (d, J=4.9 Hz, 2H), 2.68-2.58 (m, 2H), 2.55-2.44 (m, 2H), 1.84 (t, J=5.8 Hz, 2H), 1.74 (t, J=5.9 Hz, 2H). [ES+ MS] m/z 283 (MH$^+$).

Biological Activity

Measurement of Growth Inhibition of *M. tuberculosis* GFP Strains by Combination of Ethionamide (ETH) and Examples 1-11

1. Construction of Mycobacterial Recombinant Strains.
Strain *M. tuberculosis* H37Rv-GFP. A recombinant strain of *M. tuberculosis* H37Rv expressing the green fluorescent protein (H37Rv-GFP) was obtained by transformation of the integrative plasmid pNIP48 (Abadie et al., 2005; Cremer et al., 2002). In this plasmid derived from the Ms6 mycobacteriophage, the GFP gene was cloned under the strong mycobacterial promoter pBlaF and the GFP was constitutively expressed. This plasmid also contained an hygromycin resistance gene.

Strain *M. tuberculosis* W4-E1-GFP (Mutant). The *M. tuberculosis* strain E1 was a derivative of the Beijing strain W4 that was selected on ethionamide-containing agar plates (20 μg/ml). This strain carries a Gly343Ala mutation in EthA. The W4-E1 strain was transformed using pNIP48 as described above to give the fluorescent strain W4-E1-GFP.

2. Growth and Preparation of the Fluorescent Mycobacteria

Bacterial stocks kept at −80° C. were used to inoculate 5 ml of Middlebrook 7H9 medium supplemented with oleic acid-albumin-dextrose-catalase (OADC, Difco, Sparks Md., USA) and with 50 μg ml$^{-1}$ hygromycin (Invitrogen, Carlsbad, Calif. USA) in 25 cm$^2$ tissue-culture flasks. Flasks were incubated at 37° C. without shaking for 7 days. Cultures were then diluted with fresh culture medium to reach an $OD_{600}$ of 0.1. Culture flasks (75 cm$^2$) were filled with 50 ml of this diluted culture, which were cultivated 7 days at 37° C. without shaking.

3. Microplates Preparation

Ethionamide (Sigma, E6005) was diluted in DMSO at 0.1 mg/mL and 0.8 mg/ml; aliquots were stored frozen at −20° C. Test-compounds were resuspended in DMSO at a final concentration of 10 μM. Ethionamide and test-compounds were transferred to a 384-well low-volume polypropylene plate (Corning, no. 3672) and used to prepare assay plates. Ten 3-fold serial dilutions of compounds (typically in the ranges of 30 to 4.5e−3 μM) were performed into black Greiner 384-well clear bottom polystyrene plates (Greiner, no. 781091) using an Echo 550 liquid Handler (Labcyte). DMSO volume was compensated so that the concentration across all wells was equal (0.3%).

Ethionamide was then transferred to the 384-well plates, using Echo. The final concentration of ETH was 0.1 μg/ml for assays involving H37Rv-GFP, and was 0.8 μg/ml for assays involving W4-E1-GFP. The final amount of DMSO in the assay plate remained <1% v/v for each well.

Controls in the assay plate include DMSO at 0.3% (negative control) and INH at 1 μg/ml (positive control). A reference plate included rifampicin, INH and ETH ranging from 30 to 1.8e−3 μg/ml (15 points, 2× dilutions).

Cultures of H37Rv-GFP or of W4-E1-GFP to be added to assay plates were washed two times in PBS (Gibco, 14190), resuspended in fresh culture medium (without Hygromycin), and grown for 5 days at 37° C.

Finally, cultures were diluted to an OD600 nm of 0.02 (using fresh culture medium with no added Hygromycin) and 50 μL were transferred to each assay plate. Assay plates were incubated at 37° C. for 5 days. Fluorescent signal was acquired on a Victor 3 multilabel plate reader (Perkin Elmer), using exc=485 nm/em=535 nm.

Results

EC50_H37Rv measures the ability of the compounds of the invention to potentiate ethionamide activity against H37Rv strains, whereas EC50_Mutant measures the ability of the compounds of the invention to potentiate ethionamide activity against strains of TB that are resistant to ethionamide.

Examples 1 to 12 were tested essentially according to the procedure described above and all were found to have an average EC50_H37Rv of <0.75 μM and an average EC50_Mutant of <3.0 μM.

Examples 1, 2, 5 to 8, 10 and 11 had an average EC50_H37Rv of <0.20 μM and an average EC50_Mutant of <1.0 μM.

Examples 6 to 8 had an average EC50_H37Rv of <0.04 μM and an average EC50_Mutant of <0.45 μM. Example 8 had an average EC50_H37Rv of 0.038 μM and an average EC50_Mutant of 0.14 μM.

For comparison, Example 10 of WO 2014/096369 was tested in the same assay as described above and found to have an EC50_H37Rv of 0.89 μM and EC50_Mutant of 3.5 μM.

*Mycobacterium tuberculosis* In Vitro H37Rv in Human Macrophages THP-1 Inhibition Assay (Intracellular Assay)

Intracellular screening is a valuable tool for identifying new anti-tuberculosis compounds that are active in human macrophages. This ex-vivo assay may represent physiological conditions that mimic disease and take into consideration the favorable contribution of host cells. (Sorrentino, F. et al. (2016) Antimicrob. Agents Chemother. 60 (1), 640-645.)

Procedure was carried out as described in Sorrentino, F. et al. (2016) Antimicrob. Agents Chemother. 60 (1), 640-645 (supplemental material), except that before THP-1 infected cells were seeded in 384 well plates, infected macrophages were filtered in the last step of wash steps with a 40 um cell strainer to remove cell clumps and obtain single cell suspension.

The compounds of the examples were tested essentially in accordance with the above-mentioned assay (without the presence of ethionamide) and Examples 1, 2 and 4 to 10 were found to have an IC50 of less than 0.5 μM. Examples 5, 6, 7, 8 and 10 were found to have an IC50 of less than 0.1 μM. Examples 6, 7 and 8 were found to have an IC50 of less than or equal to 0.05 μM.

The invention claimed is:

1. A compound of Formula (I) or pharmaceutically acceptable salt thereof:

(I)

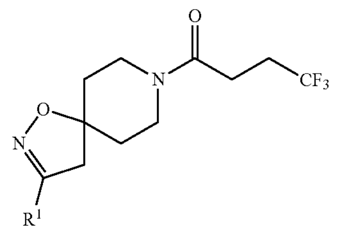

wherein $R^1$ is halogen; cyano; $C_{1-6}$ straight alkyl; $C_{3-4}$ branched alkyl; $C_{1-6}$ straight alkoxy; $C_{3-4}$ branched alkoxy; methyl substituted by one or more fluoro; ethyl substituted by one or more fluoro; methoxy substituted by one or more fluoro; or ethoxy substituted by one or more fluoro.

2. The compound or pharmaceutically acceptable salt thereof according to claim 1, wherein $R^1$ is fluoro, chloro or bromo; cyano; $C_{1-6}$ straight alkyl; $C_{3-4}$ branched alkyl; $C_{1-6}$ straight alkoxy; $C_{3-4}$ branched alkoxy; methyl substituted by one or more fluoro; ethyl substituted by one or more fluoro; methoxy substituted by one or more fluoro; or ethoxy substituted by one or more fluoro.

3. The compound or pharmaceutically acceptable salt thereof according to claim 1, wherein $R^1$ is fluoro, chloro or bromo; cyano; $C_{1-6}$ straight alkyl; $C_{3-4}$ branched alkyl; $C_{1-6}$ straight alkoxy; $C_{3-4}$ branched alkoxy; mono-, di- or trifluoromethyl; mono-, di- or trifluoromethoxy; 2-fluoroethyl; 2,2-difluoroethyl; 2,2,2-trifluoroethyl; 2-fluoroethoxy, 2,2-difluoroethoxy; or 2,2,2-trifluoroethoxy.

4. The compound or pharmaceutically acceptable salt thereof according to claim 1, wherein $R^1$ is fluoro, chloro, bromo, cyano, $C_{1-6}$ straight alkyl, $C_{3-4}$ branched alkyl, $C_{1-6}$ straight alkoxy, $C_{3-4}$ branched alkoxy, trifluoromethyl, trifluoromethoxy, 2,2,2-trifluoroethyl or 2,2,2-trifluoroethoxy.

5. The compound or pharmaceutically acceptable salt thereof according to claim 1, wherein $R^1$ is fluoro, chloro, bromo, cyano, $C_{1-6}$ straight alkyl, $C_{3-4}$ branched alkyl, $C_{1-6}$ straight alkoxy, $C_{3-4}$ branched alkoxy, trifluoromethyl, 2,2,2-trifluoroethyl or 2,2,2-trifluoroethoxy.

6. The compound or pharmaceutically acceptable salt thereof according to claim 1, wherein $R^1$ is fluoro, bromo, cyano, $C_{1-4}$ straight alkyl, $C_{1-6}$ straight alkoxy, $C_4$ branched alkoxy, trifluoromethyl, 2,2,2-trifluoroethyl or 2,2,2-trifluoroethoxy.

7. The compound or pharmaceutically acceptable salt thereof according to claim 1, wherein $R^1$ is fluoro, bromo, cyano, methyl, ethyl, trifluoromethyl, 2,2,2-trifluoroethoxy, methoxy, ethoxy, n-propoxy, iso-butoxy or hexyloxy.

8. The compound or pharmaceutically acceptable salt thereof according to claim 1 selected from:

4,4,4-trifluoro-1-[3-(2,2,2-trifluoroethoxy)-1-oxa-2,8-diazaspiro[4.5]dec-2-en-8-yl]butan-1-one;

4,4,4-trifluoro-1-(3-propoxy-1-oxa-2,8-diazaspiro[4.5]dec-2-en-8-yl)butan-1-one;

4,4,4-trifluoro-1-(3-isobutoxy-1-oxa-2,8-diazaspiro[4.5]dec-2-en-8-yl)butan-1-one;

4,4,4-trifluoro-1-(3-hexyloxy-1-oxa-2,8-diazaspiro[4.5]dec-2-en-8-yl)butan-1-one;

1-(3-bromo-1-oxa-2,8-diazaspiro[4.5]dec-2-en-8-yl)-4,4,4-trifluorobutan-1-one;

1-(3-ethoxy-1-oxa-2,8-diazaspiro[4.5]dec-2-en-8-yl)-4,4,4-trifluorobutan-1-one;

4,4,4-trifluoro-1-(3-methoxy-1-oxa-2,8-diazaspiro[4.5]dec-2-en-8-yl)butan-1-one;

4,4,4-trifluoro-1-(3-(trifluoromethyl)-1-oxa-2,8-diazaspiro[4.5]dec-2-en-8-yl)butan-1-one;

4,4,4-trifluoro-1-(3-methyl-1-oxa-2,8-diazaspiro[4.5]dec-2-en-8-yl)butan-1-one;

1-(3-ethyl-1-oxa-2,8-diazaspiro[4.5]dec-2-en-8-yl)-4,4,4-trifluorobutan-1-one;

8-(4,4,4-trifluorobutanoyl)-1-oxa-2,8-diazaspiro[4.5]dec-2-ene-3-carbonitrile; and 4,4,4-trifluoro-1-(3-fluoro-1-oxa-2,8-diazaspiro[4.5]dec-2-en-8-yl)butan-1-one.

9. The compound or pharmaceutically acceptable salt thereof according to claim 8, wherein the compound is 4,4,4-trifluoro-1-(3-(trifluoromethyl)-1-oxa-2,8-diazaspiro[4.5]dec-2-en-8-yl)butan-1-one having the following structure:

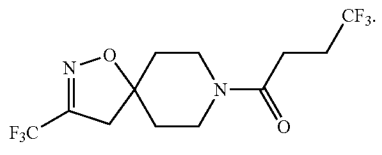

10. A method for the treatment of a mycobacterial infection in a human in need thereof, comprising administering to said human a therapeutically effective amount of the compound or a pharmaceutically acceptable salt thereof, according to claim 1.

11. A method for the treatment of a disease caused by infection with a *mycobacterium* in a human in need thereof, comprising administering to said human a therapeutically effective amount of the compound or a pharmaceutically acceptable salt thereof, according to claim 1.

12. A pharmaceutical composition comprising (a) the compound or pharmaceutically acceptable salt thereof according to claim 1; and (b) a pharmaceutically acceptable excipient.

13. A combination of (a) the compound or pharmaceutically acceptable according to claim 1 and (b) a further anti-mycobacterial agent.

14. The combination according to claim 13, wherein the further anti-mycobacterial agent is an anti-tuberculosis agent.

15. The combination according to claim 14, wherein the anti-tuberculosis agent is selected from isoniazid, rifampin, pyrazinamide, ethambutol, moxifloxacin, rifapentine, clofazimine, ethionamide, prothionamide, isoxyl, thiacetazone, rifabutin, a diarylquinoline, nitroimidazo-oxazine PA-824, delamanid (OPC-67683), an oxazolidinone, EMB analogue SQ109, OPC-167832, GSK3036656, GSK2556286, GSK3211830, a benzothiazinone, an azaindole, a dinitrobenzamide, and a beta-lactam or beta-lactam combinations.

16. The combination according to claim 13, further comprising an antiviral agent.

17. The combination according to claim 16, wherein the antiviral agent is an antiretroviral agent selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

18. A method for the treatment of tuberculosis in a human in need thereof, comprising administering to said human a therapeutically effective amount of the compound, or pharmaceutically acceptable salt thereof, according to claim 1.

19. The method according to claim 10, wherein the mycobacterial infection is a *Mycobacterium tuberculosis* infection.

20. A method for the treatment of a mycobacterial infection in a human in need thereof, comprising administering to said human (a) the compound or pharmaceutically acceptable salt thereof according to claim 1; and (b) at least one other anti-mycobacterial agent.

21. The method according to claim 20, wherein the at least one other anti-mycobacterial agent is an anti-tuberculosis agent.

22. The method according to claim 21, wherein the anti-tuberculosis agent is selected from isoniazid, rifampin, pyrazinamide, ethambutol, moxifloxacin, rifapentine, clofazimine, ethionamide, prothionamide, isoxyl, thiacetazone, a diarylquinoline, nitroimidazo-oxazine PA-824 (pretomanid), delamanid (OPC-67683), an oxazolidinone, EMB analogue SQ109, OPC-167832, GSK3036656A, GSK2556286, GSK3211830, a benzothiazinone, an azaindole, a dinitrobenzamide, and a beta-lactam or beta-lactam combination.

23. The method according to claim 20, further comprising administering to said human an antiviral agent.

24. The method according to claim 23, wherein the antiviral agent is antiretroviral agent selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

25. The compound according to claim 8, wherein the compound is 4,4,4-trifluoro-1-(3 -(trifluoromethyl)-1-oxa-2, 8-diazaspiro[4.5]dec-2-en-8-yl)butan-1-one, having the following structure:

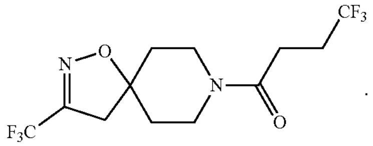 [SMILES: O=C(CCC(F)(F)F)N1CCC2(CC1)CC(C(F)(F)F)=NO2]

26. The combination according to claim 14, wherein the anti-tuberculosis agent is ethionamide.

27. A method for the treatment of tuberculosis in a human in need thereof, comprising administering to said human a therapeutically effective amount of the compound, or a pharmaceutically acceptable salt thereof, according to claim 9.

28. A method for the treatment of a mycobacterial infection in a human in need thereof, comprising administering to said human a therapeutically effective amount of the compound or a pharmaceutically acceptable salt thereof according to claim 9, wherein the mycobacterial infection is a Mycobacterium tuberculosis infection.

* * * * *